(12) United States Patent
Patel (10) Patent No.: US 8,382,695 B1
(45) Date of Patent: *Feb. 26, 2013

(54) METHOD AND APPARATUS FOR TREATMENT OF CONGESTIVE HEART DISEASE

(76) Inventor: Vinod Patel, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/797,371

(22) Filed: Jun. 9, 2010

Related U.S. Application Data (63) Continuation of application No. 11/681,533, filed on Mar. 2, 2007, now Pat. No. 7,758,531.

(60) Provisional application No. 60/778,648, filed on Mar. 2, 2006.

(51) Int. Cl.
*A61M 35/00* (2006.01)

(52) U.S. Cl. .......................... 604/4.01; 600/16

(58) Field of Classification Search ............... 604/4.01, 604/5.01, 6.11, 9, 19, 30, 32, 28, 41, 48, 604/500, 503, 505, 508; 128/898; 600/16; 623/3.1

See application file for complete search history.

(56) References Cited

U.S. PATENT DOCUMENTS

| | | | | |
|---|---|---|---|---|
| 6,514,226 | B1 * | 2/2003 | Levin et al. | 604/9 |
| 6,592,567 | B1 * | 7/2003 | Levin et al. | 604/509 |
| 7,335,192 | B2 * | 2/2008 | Keren et al. | 604/509 |
| 7,758,531 | B2 * | 7/2010 | Patel | 604/4.01 |

OTHER PUBLICATIONS

U.S. Appl. No. 11/681,533, filed Mar. 2, 2007, Patel.
U.S. Appl. No. 60/778,648, filed Mar. 2, 2006, Patel.
Non-final rejection issued Sep. 22, 2009 by the USPTO for U.S. Appl. No. 11/681,533, filed Mar. 2, 2007 (Inventor—Patel) (7 pages).
Response to non-final rejection filed Dec. 22, 2009 with the USPTO for U.S. Appl. No. 11/681,533, filed Mar. 2, 2007 (Inventor—Patel) (10 pages).
Examiner interview summary filed Mar. 17, 2010 with the USPTO for U.S. Appl. No. 11/681,533, filed Mar. 2, 2007 (Inventor—Patel) (4 pages).
Notice of allowance issued Apr. 7, 2010 with the USPTO for U.S. Appl. No. 11/681,533, filed Mar. 2, 2007 (Inventor—Patel) (4 pages).
Issue notification issued Jun. 30, 2010 with the USPTO for U.S. Appl. No. 11/681,533, filed Mar. 2, 2007 (Inventor—Patel) (1 page).

* cited by examiner

*Primary Examiner* — Tatyana Zalukaeva
*Assistant Examiner* — Benedict L C Hanrahan
(74) *Attorney, Agent, or Firm* — Ballard Spahr LLP (57) ABSTRACT

In one aspect, the present invention is directed to an apparatus and method for treating congestive heart failure that restores kidney renal functions by artificial perfusion of at least one kidney. In one aspect, a catheter inserted into the aorta of the patient has an outlet port that supplies the patient's blood obtained from a patient's aorta into an adjoining renal artery of the patient to perfuse the kidney. The catheter comprises a rotor housed inside a portion of the catheter to supply the blood to the kidney at a desired pressure. The restoration of kidney function assists the heart by removing excess fluid, urine and toxin from the patient, and by normalizing the patient's renin-angiotensin system and other neurohormonal substances.

16 Claims, 8 Drawing Sheets

METHOD AND APPARATUS FOR TREATMENT OF CONGESTIVE HEART DISEASE

This application is a continuation application of U.S. Utility application Ser. No. 11/681,533, filed Mar. 2, 2007, which claims the benefit of U.S. Provisional Patent Application No. 60/778,648, filed on Mar. 2, 2006, which is incorporated in its entirety in this document by reference.

FIELD OF THE INVENTION

The present invention relates to methods and apparatus for treating congestive heart disease and, more particularly, for a method and apparatus to normalize kidney perfusion to restore and enhance renal function.

BACKGROUND OF THE INVENTION

Heart failure is a growing and dominant public health problem in the United States. Literally, millions of patients in this country suffer from heart failure and more than half a million patients are newly diagnosed with heart failure every year. The heart failure patient pool is continuing to grow at an increasing rate partly because of early recognition and better treatment coupled with "salvage" of patients with acute myocardial infarctions earlier in life. Heart failure is the most common Medicare DRG group and more Medicare dollars are spent for the diagnosis and treatment of heart failure than for any other diagnosis. The costs of heart failure treatment can be dramatically reduced by decreasing hospital stay alone.

The patho-physiology of heart failure involves changes in cardiac function, neuro-humoral status, blood volumes, and systemic vascular resistance. A primary change in cardiac function precipitates changes in neuro-humoral status, blood volume and vascular resistance. These changes can neutralize cardiac dysfunction up to certain limits. Therefore, some of the most effective conventional treatments for chronic heart failure involve modulating non-cardiac factors such as modifying renal and vascular function.

In regard to cardiac changes, systolic dysfunction, diastolic dysfunction, or combination of both can result in decline in stroke volume. Ischemic cardiomyopathy is the most common cause of chronic heart failure. For neuro-humeral changes, arterial and venous vasoconstriction and increases in blood volume, as a result of sympathetic activation and renin-angiotensin system, increased anti-diuretic hormone/vasopressin, and atrial-natriuretic peptide, try to compensate for the decline in cardiac output. However, this paradoxically affects cardiac function further by increasing both ventricular afterload and preload. Factors such as nitric oxide and endothelin, both of which are increased in heart failure, may play a role in the pathogenesis of heart failure. GFR becomes dependent on afferent arteriolar flow in the most severe heart failure, despite stimulation of hormonal and homodynamic pathways, which would normally increase efferent arteriolar tone.

Arterial and venous constriction as a result of sympathetic activation is also enhanced by humoral activation via, for example, the renin-angiotensin system and antidiuretic hormones, such as, for example, vasopressin. Further, a compensatory increase in blood volume serves to increase ventricular preload and thereby enhance stroke volume by the Frank-Starling mechanism.

Figure 6:
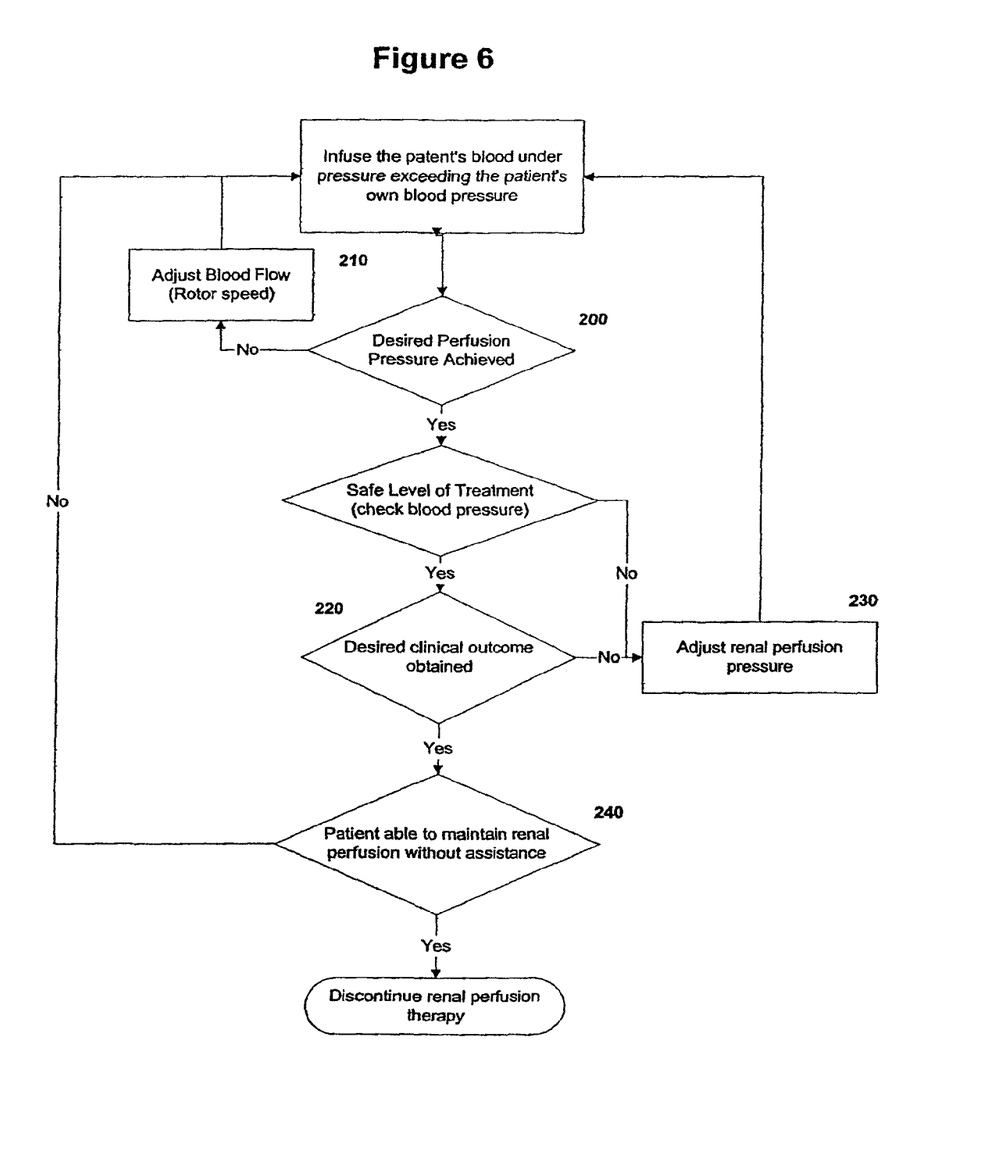
FIG. 6 is a flow chart for another embodiment of a method of perfusing a patient's kidney to achieve a desired condition of the patient.

One will appreciate that blood volume can be augmented by a number of mechanisms. For example, reduction of renal blood flow results in decreased urine output and retention of fluid. Furthermore, a combination of reduced renal perfusion and sympathetic activation of the kidneys activates the renin-angiotensin system, which, in turn, enhances aldosterone secretion. Still further, increases in circulating arginine vasopressin (antidiuretic hormone) contributes to renal retention of water. As a result, final outcome of humoral activation is an increase in renal reabsorption of sodium and water. The resultant increase in blood volume helps to maintain cardiac output; however, this increase can be deleterious because it raises venous pressures, which can lead to pulmonary and systemic edema. FIG. 6 summarizes the compensatory mechanisms described above.

As noted above, it is well known that cardiac dysfunction induces a series of events that ultimately contribute to congestive heart failure. Reductions in renal blood flow due to reduced cardiac output can, in turn, result in the retention of excess fluid in the patient's body, leading for example, to pulmonary and cardiac edema. The vicious cycle of fluid and electrolytes retention increases the work of the compromised heart.

In a healthy adult, kidneys are perfused by about 20 to 22% of cardiac output, which typically results in around 60,000 cc of blood circulating through kidneys per hour. Chapter 62 of Heart Disease: A Textbook of Cardiovascular Medicine, (E. Braunwald, ed., 5th ed. 1996), published by Saunders, Philadelphia, Pa., reports that for patients with congestive heart failure, the fall in effective renal blood flow is proportional to the reduction in cardiac output. Renal blood flow in normal patients in an age range of 20-80 years averages 600 to 660 ml/min/m$^2$, corresponding to about 14 to 20% of simultaneously measured cardiac output. Within a wide spectrum of CHF severity, renal blood flow is depressed to an average range of 250 to 450 ml/min/m$^2$.

Thus, in acute decompensation, it is beneficial to improve renal perfusion. In view of the foregoing, it would be desirable to increase renal profusion by positioning a catheter below the renal artery. This would beneficially result in an increase in laminar flow in the aorta and a decrease in the serum levels of vasoconstrictors. Thus, improvements in renal circulation as well as laminar flow in the aorta can be achieved.

It further would be desirable to provide methods and apparatus for treating and managing heart failure without administering high doses of drugs or dehydrating the patient. It further would be desirable to provide methods and apparatus for treating and managing heart failure by improving blood flow to the kidneys, thereby enhancing renal function. It also would be desirable to provide methods and apparatus for treating and managing heart failure that permit the administration of low doses of drugs, in a localized manner, to improve renal function.

SUMMARY

In view of the foregoing, it is an object of the present invention to provide methods and apparatus for treating and managing congestive heart failure without administering high doses of drugs or dehydrating the patient.

It is another object of this invention to provide methods and apparatus for treating and managing congestive heart failure by improving blood flow to the kidneys, thereby enhancing renal function.

It is also an object of this invention to provide methods and apparatus for treating and managing congestive heart failure that permit the administration of low doses of drugs, in a localized manner, to improve renal function.

It further is an object of the present invention to provide methods and apparatus for treating and managing congestive heart failure using apparatus that may be percutaneously and transluminally implanted in the patient.

Figure 7:
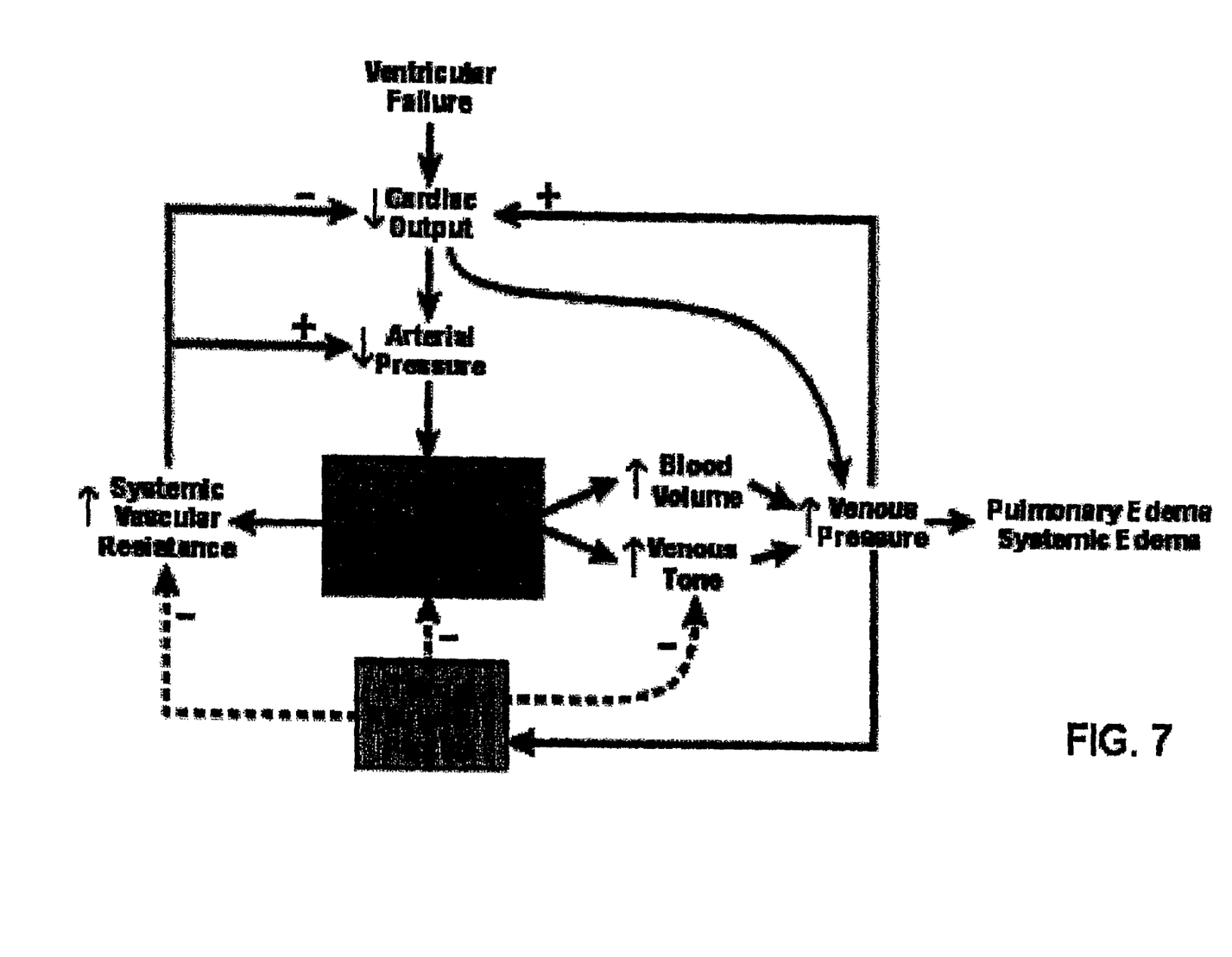
FIG. 7 is a flow diagram of the compensatory cycle of congestive heart failure.

These and other objects of the present invention are accomplished by providing a novel method and apparatus of treating acute and chronic congestive heart failure by restoration of renal perfusion pressure. Restoration of acceptable blood pressure applied directly applied to one or both kidneys of a patient with heart failure significantly improves renal blood flow, removes excess body fluids and improve the patient's overall condition. In addition, restoring renal perfusion pressure to the kidney suppresses the deleterious activation of the renin-angiotensin system and the consequences of its widespread adverse effects on heart failure patients as is shown in FIG. 7. Increased fluid removal results from the restoration of a hydrostatic gradient across the kidney by increasing renal blood flow under increased renal perfusion pressure. The level of effectiveness of this method is substantially above the levels achieved by drug therapy.

Figure 8:
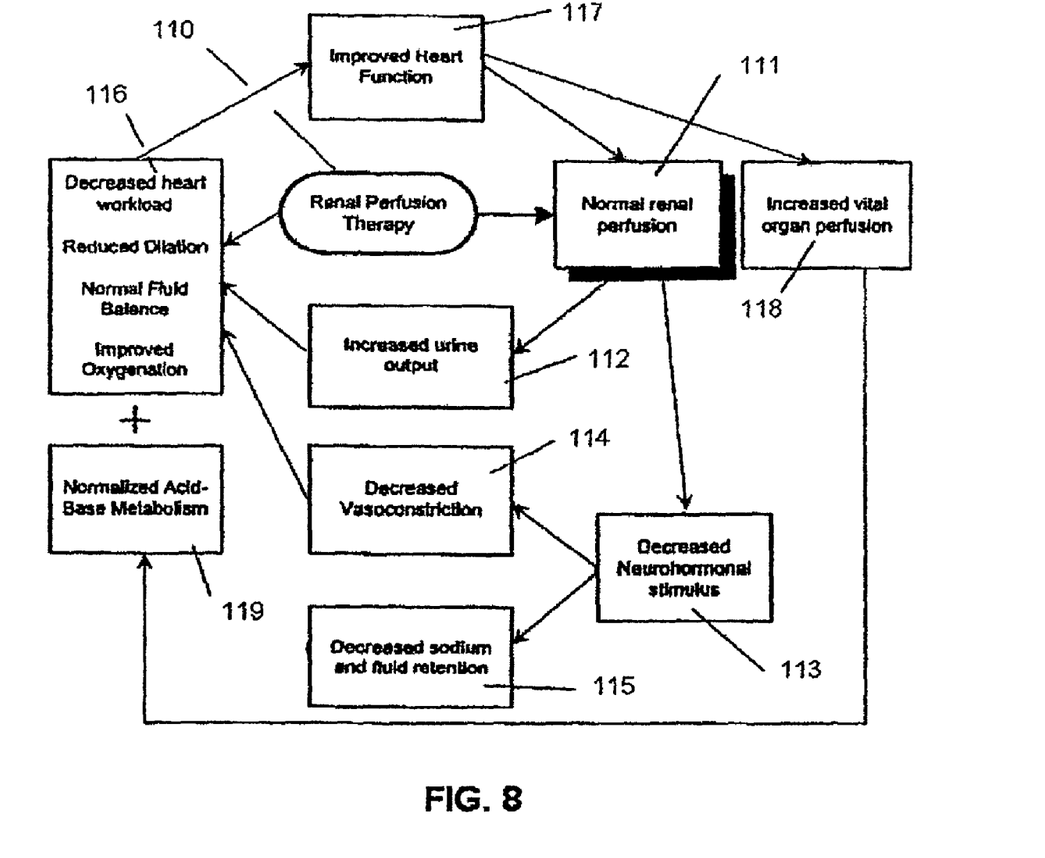
FIG. 8 is a flow diagram of the remedial effects of direct renal perfusion therapy on the cycle of congestive heart failure.

As shown in FIG. 8, restoring renal perfusion 111, should result in increased urine output 112 and a decrease in the neurohormaonal stimulation 113 caused by kidneys in a failing condition. This decrease in stimulation by the kidneys is expected to decrease the vasoconstriction 114 in the patient's circulatory system, and decrease the amount of sodium and fluid retention 115 in the patient. In turn, increased urine output, reduced vasoconstriction, and decreased sodium level should restore normal fluid balances in the patient, improve oxygenation of the blood and decrease the heart workload 116. Heart function should improve 117 due to the reduction in its workload and the other beneficial effects due to renal perfusion. Moreover, a stronger heart and higher blood pressure will improve the perfusion of other organs 118 and thereby normalize the acid-base metabolism 119 to further improve the workload on the heart. The system for treating congestive heart failure disclosed herein restores kidney functioning and thereby breaks the cycle between heart and kidney failure.

In one embodiment of the present invention, a renal pump catheter system is provided that is configured to provide a pressurized blood flow that is adequate to perfuse the kidney and rapidly restores adequate kidney functions to the kidney. In one aspect, the renal pump catheter system comprises a catheter that is operatively coupled to a power source for pumping fluid at a desired pressure into a renal artery of the patient. In one embodiment, the catheter comprises a conduit, an inlet region, an outlet region and a lumen. The inlet region defines at least one inlet port and has a first end that is connected to a distal end of the conduit. The outlet region defines an outlet port. In one aspect, the lumen extends between the at least one inlet port and the outlet port.

In one embodiment, the catheter further comprises an axially rotatable rotor that is mounted therein the inlet portion downstream of the at least one inlet port and is configured for selective rotation to pump blood from the at least one inlet port, through the lumen, and out of the outlet port at a desired rate of speed and at a desired pressure. In one aspect, the catheter further comprises a wire that is coupled to the bottom end of the rotor such that rotation of the wire imparts a complementary rotation of the rotor. In one aspect, the wire is sheathed at least partially by the conduit. In another aspect of the catheter system, a power source is provided that is operatively coupled to the wire for selective and controlled rotation of the wire.

In operation, the inlet region is configured for placement in a source of arterial blood, such as an aorta adjacent to the selected renal artery, and an outlet region having at least one conduit configured to be placed in a renal artery. As noted above, the lumen is adapted to allow passage of arterial blood directly into a renal artery. The catheter may also include means for engaging an interior surface of the renal artery to retain the catheter in position relative to the renal artery, and may comprise an occluder that reduces retrograde backflow of blood exiting the outlet port back into the abdominal aorta. In one aspect, the catheter is configured to permit percutaneous, transluminal implantation.

Other apparatus, methods, and aspects and advantages of the invention will be discussed with reference to the Figures and to the detailed description of the preferred embodiments.

BRIEF DESCRIPTION OF THE DRAWINGS

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DETAILED DESCRIPTION OF THE INVENTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "surface" includes aspects having two or more such surfaces unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The present invention may be understood more readily by reference to the following detailed description of preferred embodiments of the invention and the examples included therein and to the Figures and their previous and following description.

Figure 1:
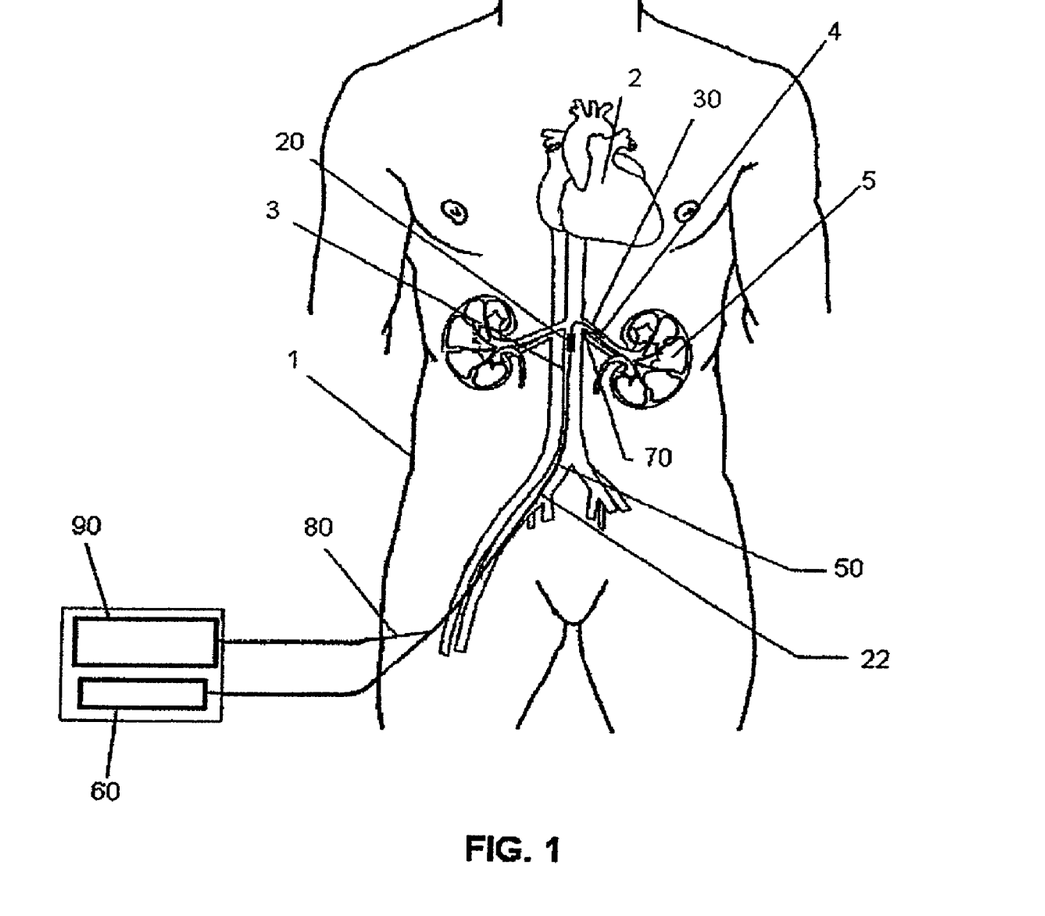
FIG. 1 is a graphical illustration of a patient being treated for heart failure by perfusing a kidney with the renal pump catheter system of the present invention.
Figure 2:
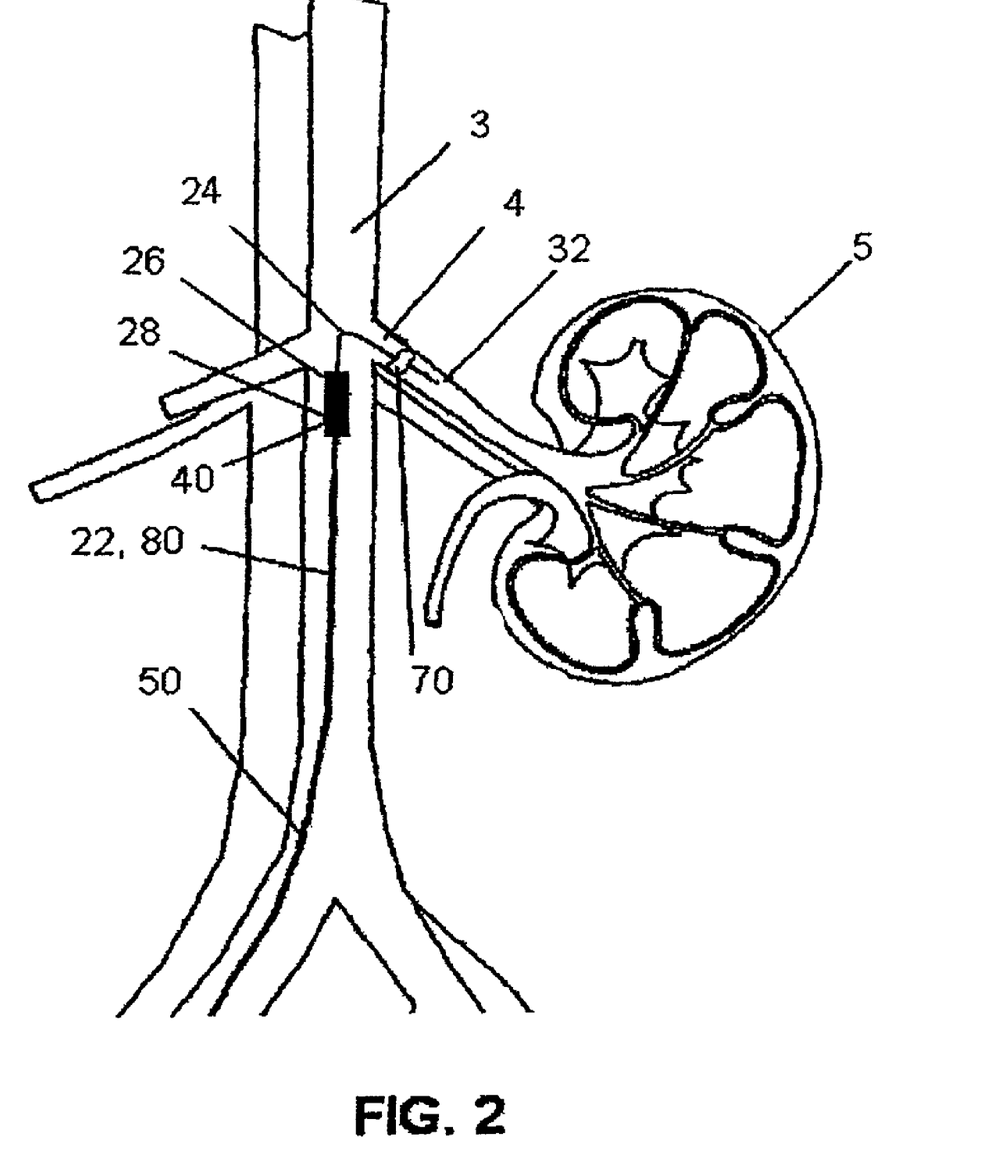
FIG. 2 is an enlarged schematic diagram showing a renal pump catheter positioned therein a renal artery of a patient.

FIG. 1 is a schematic diagram of a patient 1 suffering from congestive heart failure and his heart 2 is unable to maintain sufficient blood pressure in his circulatory system to maintain normal kidney functions. Due to the failing heart, blood flowing from the aorta 3 into the renal artery 4 lacks sufficient pressure to be filtered through the kidney. If the congestive heart failure is acute and the patient requires immediate treatment, then a clinical in-situ kidney perfusion catheter apparatus may be used to increase the blood pressure in the renal artery and perfuse the kidney with blood.

Referring to FIGS. 1-4, the renal pump catheter system 10 of the present invention pumps blood directly into the renal artery at sufficient pressure and volume to perfuse at least portion of the kidney and to restore at least a nominal amount of the patient's kidney function. This method of artificially perfusing the kidney with the renal pump catheter system treats congestive heart failure by (i) restoring nominal kidney function, (ii) reducing fluid build-up in the body, (iii) cleansing the blood of salt, urine and other toxins, (iv) reducing the output by the kidney of neurohormonal distress signals causing vasoconstriction in the patient's circulatory system, e.g., blood vessels, and (v) reducing pumping demands on the heart by providing supplemental blood pressure via the renal cathether pump.

In one aspect, blood is withdrawn from the patient's aorta proximate to the renal artery of the selected kidney. The blood is conducted via an axial rotor rotatably mounted therein a renal pump catheter that is that is capable of raising the pressure of the blood to the desired value. In operation, the axial rotor elevates the blood pressure and ejects blood out of an outlet port of the renal pump catheter. The outlet port is placed in the patient's renal artery using common fluoroscopic technique or using a permanently implanted graft.

An exemplary renal pump catheter 20 of the catheter system 10 is operatively coupled to a power source 60 for pumping fluid at a desired pressure into a renal artery 4 of the patient. In one embodiment, the renal pump catheter 20 comprises a conduit 22, an inlet region 26, an outlet region 30 and a lumen 36. The inlet region defines at least one inlet port 28 and has a first end 29 that is connected to a distal end 24 of the conduit 22. The outlet region 30 defines an outlet port 32 and is connected and extends therefrom the inlet region. In one aspect, the lumen 36 extends between the at least one inlet port 28 and the outlet port 32.

Figures 3A, 3B, 3C:
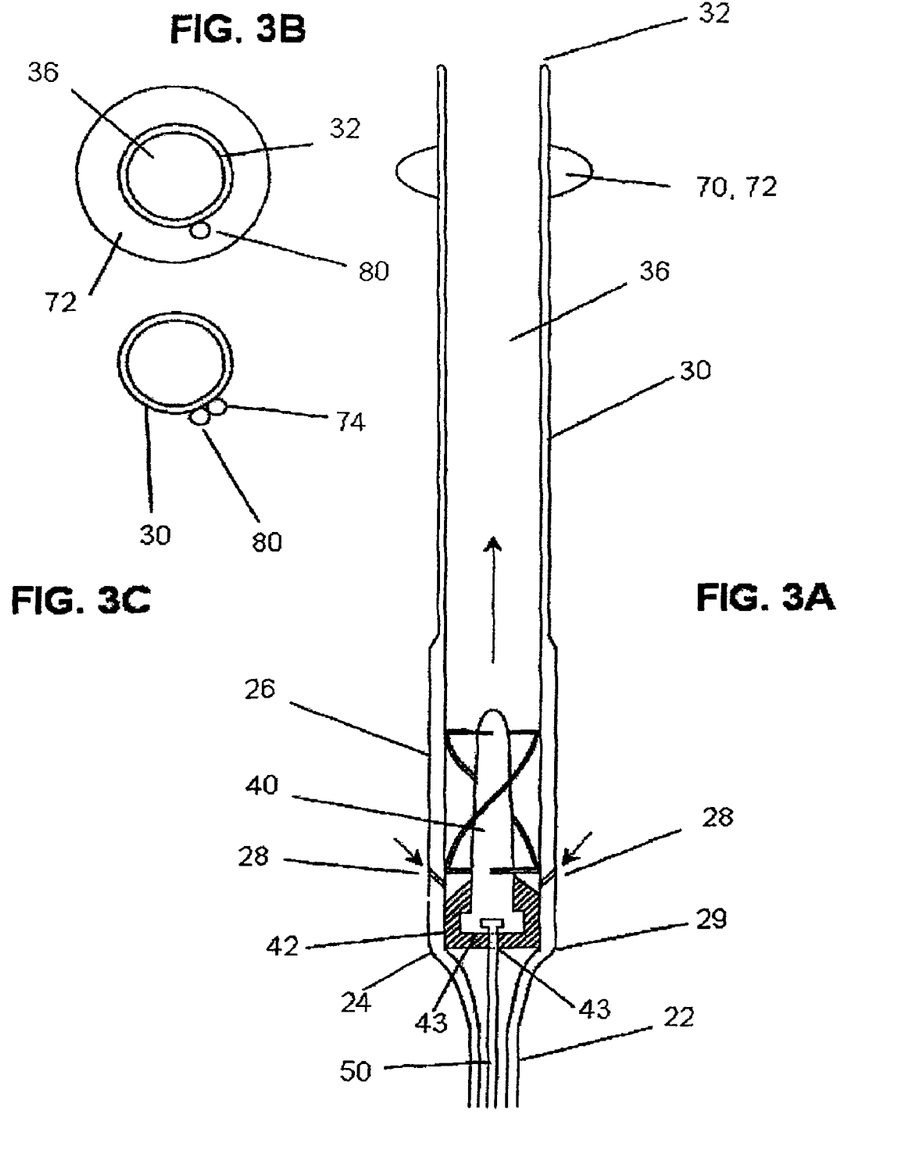
FIG. 3A is a partial cross-sectional view of one embodiment of the renal pump catheter of the present invention.
FIG. 3B is a top elevational view of the distal end portion of the outlet region of the renal pump catheter of FIG. 3A.
FIG. 3C is a exemplified cross-sectional view of an intermediate portion of the outlet region of the renal pump of FIG. 3A, showing a pressure line and a lumen in communication with the occluder of the catheter.

As noted above, the catheter 20 further comprises an axially rotatable rotor 40 that is mounted therein the inlet portion of the catheter downstream of the at least one inlet port. The rotor 40 is configured for selective rotation to pump blood from the at least one inlet port 28, through the lumen 36, and out of the outlet port 32 at a desired rate of speed and at a desired pressure. In another aspect, the catheter further comprises a mount 42 that is positioned therein first end of the inlet region and is configured to prevent retrograde blood flow into the conduit 22 from the inlet region 26. The mount 42 and rotor 40 are further configured for selective rotational movement about a longitudinal axis of the mount.

In another aspect, the renal pump catheter 20 further comprises a wire 50 that is coupled to a bottom end 41 of the rotor via a bore 43 defined in the center of the mount such that rotation of the wire imparts a complementary rotation of the rotor. In one aspect, the wire 50 is sheathed at least partially by the conduit 22. In another aspect of the renal pump catheter system, the power source 60 is operatively coupled to the wire for selective and controlled rotation of the wire, which results in selective and complementary rotation of the rotor. In an alternative, embodiment, it is contemplated that the rotor can be rotated via a motor that can exemplarily be positioned adjacent to the rotor.

Figure 4:
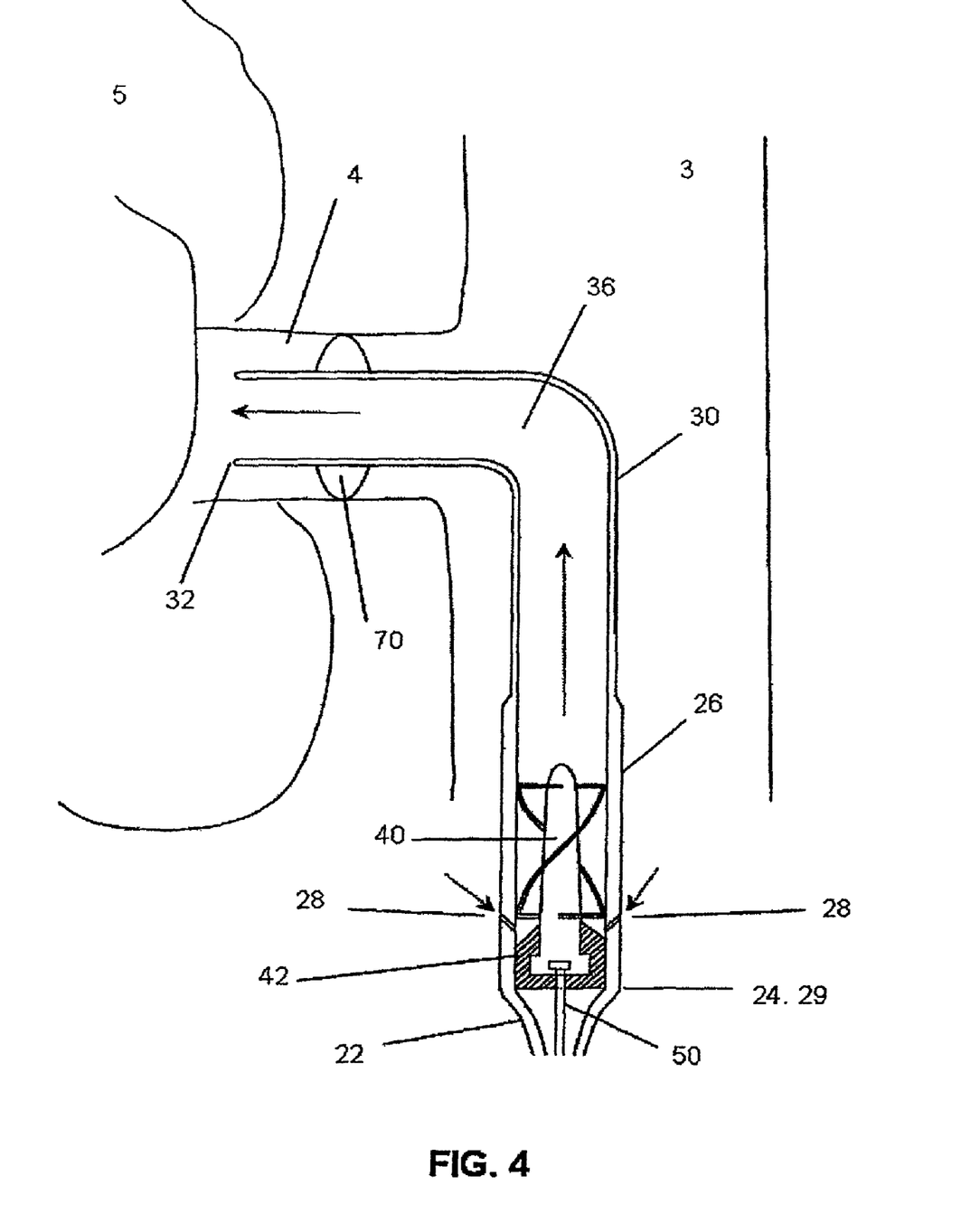
FIG. 4 is a exemplified schematic view of the renal pump catheter of FIG. 3A positioned therein the renal artery for pressurized perfusion of the kidney.

In operation, as the renal pump catheter 20 is moved by a surgeon from the insertion point at the groin and through the femoral artery, into the aorta 3, it makes a turn at the renal artery branch, passes through the ostium and into the renal artery 4. The inlet region is configured for placement in a source of arterial blood, such as an aorta adjacent to the selected renal artery, and the outlet region containing the outlet port is configured to be placed in a renal artery. As noted above, the lumen is adapted to allow passage of arterial blood directly into a renal artery.

The catheter may also include means for engaging an interior surface of the renal artery to retain the catheter in position relative to the renal artery, and may comprise an occluder 70 that reduces retrograde backflow of blood exiting the outlet port back into the abdominal aorta. In one aspect, the renal pump catheter can comprise a conventional sealing balloon 72 mounted on the exterior of the outlet region of the catheter between the outlet port of the outlet region and the at least one inlet port that can be selectively expanded to block or occludes the renal artery during perfusion, so as to prevent reverse blood flow from the outlet port out the renal artery and into the aorta. In this aspect, the renal pump catheter can further comprise an occluder lumen 74 in communication with the sealing balloon so that the sealing ballon can be selectively inflated to a desired pressure and size. In another aspect, a least a portion of the surface of the balloon 72 can have male protrusions extending therefrom that are configured to secure the catheter 20 into the desired position and aids in insuring that the balloon forms a leak proof connection with the wall of the artery to prevent retrograde blood flow. In this aspect, the male protrusions can have a fin-like shape.

Optionally, the occluder 70 can comprise a low density, biocompatible sponge-like material that may be compressed to a small thickness, and that absorbs and expands when exposed to body fluid. In operation, this exemplary occluder preferably is compressed to a small thickness and then mounted on the outlet region of the renal pump catheter so that, when the occluder is deployed in a renal artery, it swells and engages the interior of the renal artery.

In various aspects, it is contemplated that the conduit 22 and the outlet region 30 of the renal pump catheter are flexible. In another aspect, it is contemplated that the inlet region 26 of the catheter is less flexible than the outlet region. In one aspect, the portions of the renal pump catheter that form the inlet region can have a thicker wall thickness than the portions of the renal pump catheter that form the outlet region. In a further aspect, portions of the renal pump catheter that form the conduit 22 can have a thinner wall thickness than the portions of the renal pump catheter 20 that form the inlet region 28.

Blood, at a higher pressure than provided by the patient's heart, is supplied to the lumen 36 via the at least one inlet holes 28 and is ejected into the renal artery 4 from the outlet end 32 of the renal pump catheter 20 by means of the rotating rotor 40 mounted therein the renal pump catheter. One skilled in the art will appreciate that the blood ejected from the outlet port of the renal pump catheter increases the pressure of the blood flowing through the renal artery to the kidney. Using the renal pump catheter system of the present invention, the blood flow entering the kidney 5 has sufficient flow and pressure to cause the kidney to resume normal functioning (or at least adequate functioning), including removing excess body fluids, sodium and other toxins, and increasing urine flow.

In one aspect, the renal pump catheter 20 of the present invention is configured to permit percutaneous, transluminal implantation. In another aspect, for patients that need continuous congestive heart failure treatment to keep their kidneys perfused adequately and potentially to reverse the heart failure state, an implantable or partially implantable electrical motor [not shown] operatively coupled to the wire or, alternatively, directly to the rotor, can be surgically positioned in the patient in a manner similar to the implanting of other conventional power sources.

After the renal pump catheter 20 is positioned therein the renal artery, the wire 50 is coupled to the power source 60 and a physician turns on the power source. Blood is introduced into the patient's renal artery under pressure controlled by the operator. This pressure will determine the desired GFR and urine output. The physician may desire to adjust the perfusion pressure based on clinical information to optimize the treatment. Alternatively, clinical data could be input directly into the renal pump catheter system equipped with a computer 90 that is programmed to optimize the treatment. Exemplary clinical data could include, but is not limited to, the systemic blood pressure, cardiac output, central venous blood pressure (CVP), blood oxygen saturation, urine output, GFR, other hematological or biochemical parameters, and patient's weight. The preferred parameter to monitor for control of the renal pump system 10 of the present invention is the pressure of the fluid proximate the outlet port 32 of the catheter 20, which is the blood pressure within the renal artery proximate the outlet port. In one aspect, the renal pump catheter 20 further comprises a pressure sensor in communication with the distal end of the outlet region of the renal pump catheter, which is adapted to feedback the system. In one aspect, the renal pump catheter 20 comprises a pressure sensor lumen 80 that extends to the distal end of the outlet region of the catheter. In alternative aspects, it is contemplated that an open or closed loop control could be used to maintain the pressure of the fluid proximate the outlet port of the renal pump catheter at the desired pressure by modulating, as required, the relative rotational speed of the axial rotor.

In one aspect, the pressure of the blood delivered to the outlet port 32 is controlled such that the pressure is within a normal autoregulatory range of a perfusion pressure for the kidney. In an alternative aspect, the pressure of the blood delivered to the outlet port 32 is controlled such that the pressure is higher than the normal autoregulatory range but lower than the pressure that will cause barotrauma of the kidney.

One objective is to remove fluid from the patient as fast as is safe while also protecting the patient's kidney. It is commonly known from the use of diuretics and hemofiltration in acute heart failure patients that there is danger in removing fluid too rapidly. The significant amount of extra fluid that burdens heart failure patients is stored in the space outside of the blood vessels, e.g., in the tissue, and cannot be mobilized quickly.

Heart failure patients require a certain amount of preload or heart filling pressure for their weakened heart to pump adequate amounts of blood. These factors dictate that the unwanted fluid shall be removed from these patients slowly with care as to not make them hypotensive. Information about hypotension can be derived from mean arterial pressure based on absolute values of the patient's previous history.

In one exemplary aspect, the physician inputs the desired renal arterial blood pressure and the renal pump catheter system 10 adjusts the renal perfusion pressure slowly to remove fluid at the rate that will result in the desired pressure. In another exemplary aspect, the physician could command the system to remove a set amount of fluid from the patient over a set number of hours at the maximum safe rate. The physician can adjust that target based on the a number of patient parameters such as, for example, the patient's blood pressure or weight measurements. Since the response of each patient's kidney to pressure will be different, the patient's weight will need to be monitored, or more conveniently, the system can be equipped with means to measure the weight or volume of excreted urine.

The method for treating congestive heart failure described herein may be used to stabilize, improve or restore normal or adequate kidney function in the setting of low blood pressure and flow, in particular allowing enhanced patient fluid removal, modulation of the renin-angiotensin system and other neurohormonal substances, treatment of, improvement in or prevention of the occurrence of congestive heart failure. The system 10 of the present invention can refer to any temporary or permanently fully or partially implantable perfusion system used in the treatment of heart failure. In one alternative aspect, using the methodologies described herein, two renal pump catheters can be inserted into the renal arteries via, for example, separate percutaneous incisions in both femoral arteries, so that both kidneys can be perfused simultaneously.

In a further aspect, the renal pump catheter 20 further comprises a second lumen extending from exterior of the patient's body to the distal portion of the outlet portion of the renal pump catheter. The second lumen is adapted to allow physicians to add therapeutic agents directly to the blood stream being perfused under pressure in the kidney. This ability to introduce therapeutic agents to the blood flow allows physicians to maintain, improve, or help restore kidney or overall circulatory function. Such agents may include, for example and not meant to be limiting, diuretics and vasodilators or be one or more other therapeutic agents, selected from the group consisting of angiotensin converting enzyme (ACE) inhibitors, beta-blockers, cardiac glycosides and/or other commonly known pharmacological or mechanical therapeutic modalities. Significantly, they can be introduced into the blood system in much smaller dosages than would be required if the medicine was given systemically. In this way, the beneficial effects of the treatment can be achieved minimizing any deleterious side effects or toxicity.

Figure 5:
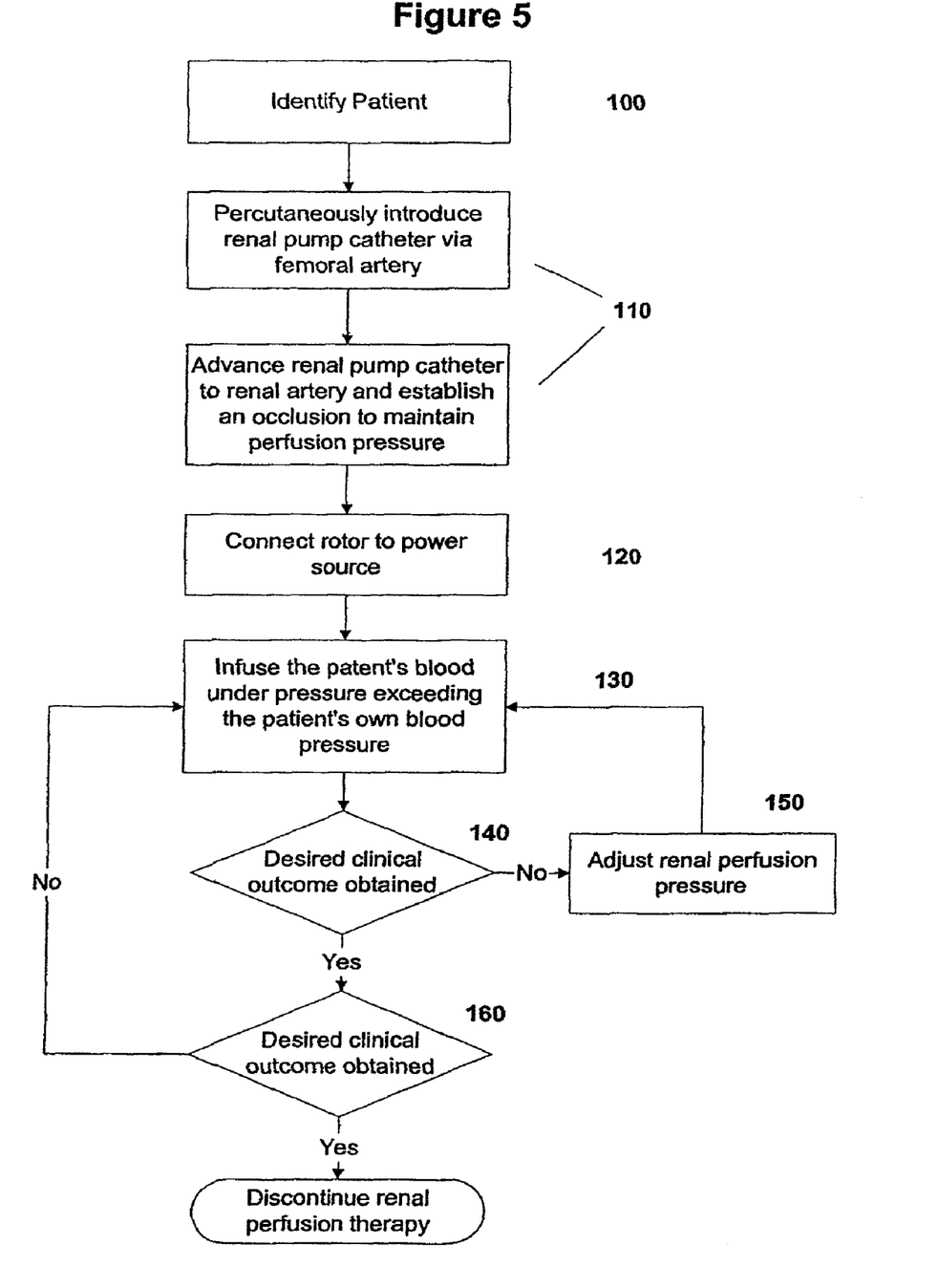
FIG. 5 is a flow chart for a method of perfusing a patient's kidney to achieve a desired condition of the patient.

FIG. 5 is a flow chart for a method of perfusing a patient's kidney to achieve a desired condition of the patient. The patient with congestive heart failure is identified, in step 100, and prepared for percutaneous introduction of the renal pump catheter 20 or needle via a femoral artery or graft tunnel at step 110. Once inserted, the outlet region of the renal pump catheter is advanced to a renal artery 4 to establish fluid connection and maintain perfusion pressure to the kidney 5. At this step, seals and occlusion devices are activated to form the alternative fluid path though the lumen of the renal pump catheter. Further, in this step, the at least one inlet port is positioned in an adjacent aorta. At 120, the wire is connected to the power source and the power source is turned on to allow infusion of the patient's own blood under a pressure via the renal pump catheter. Once the pressurized fluid communication is established, perfusion pressure will be adjusted to restore the filtration functions of the kidney and augment blood pressure up to the autoregulatory range of the patient's kidney, at 130. At 140, the patient will be monitored to determine if the desired clinical outcomes of removing the desired amount of fluid over the desired time, improving glomerular filtration rate, increasing urine output, blood pressure and decreasing the compensatory response mechanisms of the rennin angiotensin system are obtained. If the desired clinical outcomes are not achieved, renal perfusion pressure will be adjusted at a step 150. At 160, if the patient is able to maintain renal perfusion without the assistance of the renal perfusion pump and apparatus, then renal perfusion therapy is discontinued.

Referring to FIG. 6, a flow chart is presented that discloses an alternative embodiment in which a desired renal pressure and/or a desired clinical outcome are predetermined. In step 200, the method first determines whether the predetermined perfusion pressure has been achieved. Pressure sensors in communication with the distal end of the outlet region of the renal pump catheter may measure a flow pressure which can be converted to an estimated renal perfusion pressure, using standard fluid dynamic algorithms that take into account the viscous effects of the perfusion catheter on the flow of blood to the renal artery. If the calculated perfusion pressure does not fall within an acceptable range of the predetermined pressure, for example 100 mm Hg+/−10 mmHg, then the speed of rotation of the axial rotor is adjusted to achieve the desired perfusion pressure, in 210. It is believed that until the desired renal pressure is achieved, that normal kidney functions will not result. Accordingly, steps 200 and 210 ensure that the proper fluid pressure is applied to perfuse the kidney such that the kidney will resume its normal filtering function.

Once an appropriate safe level of perfusion pressure is achieved, then the patient is monitored for urine output, fluid status, edema, pulmonary wedge pressure or other desired clinical outcome in 220. The computer 90 that is a part of the renal pump catheter system 10 can perform such monitoring. Alternatively, the operator can make measurements and enter them into the system via a conventional input device, such as, for example, a keyboard. For example, blood pressure can be monitored every second using common blood pressure monitor, while urine output (by weighting the urine collection bag) can be measured every ten minutes. In another aspect, the patient's weight can be monitored every four hours to correct other measurements.

If the desired clinical outcome is not achieved within a predetermined period of time, e.g., four to eight hours, then desired (or predetermined) perfusion pressure to the kidney is readjusted in hopes of restoring kidney function, in 230. For example, the desired pressure may be incrementally increased by 10 or 20 mmHg. Each time the perfusion pressure is adjusted, the method first checks that the measured renal perfusion pressure matches the current setting of the desired perfusion pressure. Once the perfusion pressure is properly set, then the method monitors the patient for a safe limit then for a desired clinical outcome.

One skilled in the art will appreciate that renal blood flow is regulated by neurohormonal feedbacks of the body within a broad range of 200 to 600 mL/min. Vascular resistance of the kidney can be expected to change continuously. The servomechanism of the power source will maintain perfusion pressure on target by manipulating the rotor speed while allowing the kidney to adjust to the changing neurohormonal milieu.

Once the desired clinical outcome is reached, e.g., sufficient volume of fluid has been removed, then the patient is checked for whether he can maintain renal perfusion without assistance, in 240. To determine whether the patient can naturally maintain urine output, a doctor may temporarily discontinue or markedly reduce the blood pump after determining that the kidneys have achieved the desired clinical effect, e.g., urine flow, blood pressure, or fluid volume with artificial perfusion. If the patient maintains the desired clinical outcome for some minimum period, e.g., four to eight hours during which an adequate amount of urine flow continues, then the doctor can discontinue perfusion treatment to the patient. If the patient does not maintain the desired clinical outcome after artificial perfusion is stopped, the artificial perfusion of the kidney can continue.

Once the kidney begins normal functioning and reduces the load on the heart by eliminating excess body fluid and blood toxins, the heart may be unloaded sufficiently to naturally increase the blood pressure to the kidneys at a level sufficient to sustain kidney functioning. In that case, the treatment has succeeded and the patient can be removed, at least temporarily, from artificial perfusion devices and treatment. In other cases a patient may require another treatment in several weeks or months.

One would appreciate that it is contemplated that the outlet region of the catheter can be bifurcated into two lumens that are configured for operative receipt into both renal arteries for perfusion of both kidneys. Also, the catheter can be inserted into incisions made in other vessels as selected by the physician. Further, the system of the present invention can be use to pressurize blood flow in any select blood vessel for pressurized delivery of blood to any select organ.

The preceding description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. The corresponding structures, materials, acts, and equivalents of all means or step plus function elements in the claims below are intended to include any structure, material, or acts for performing the functions in combination with other claimed elements as specifically claimed.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Accordingly, those who work in the art will recognize that many modifications and adaptations to the present invention are possible and can even be desirable in certain circumstances and are a part of the present invention. Other embodiments of the invention will be apparent to those skilled in the art from consideration of the specification and practice of the invention disclosed herein. Thus, the preceding description is provided as illustrative of the principles of the present invention and not in limitation thereof. It is intended that the specification and examples be considered as exemplary only, with a true scope and spirit of the invention being indicated by the following claims.

What is claimed is:

1. A renal pump catheter system for perfusing a kidney of a patient with the patient's blood, comprising:
    a catheter comprising:
        a conduit;
        an inlet region defining at least one inlet port, a first end of the inlet port connected to a distal end of the conduit;
        an outlet region defining an outlet port;
        a lumen extending between the at least one inlet port and the outlet port;
        a rotor mounted therein the inlet portion proximate the at least one inlet port, wherein the rotor is configured for selective rotation to pump fluid at a desired pressure from the at least one inlet port and out of the outlet port; and
        a wire connected to the bottom end of the rotor such that rotation of the wire imparts a complementary rotation of the rotor, wherein the wire is sheathed at least partially by the conduit; and
    a power source operatively coupled to the wire,
    wherein the catheter is configured for percutaneous and transluminal advancement along a guidewire such that the at least one inlet port is disposed in a source of arterial blood proximate the patient's renal artery;
    wherein at least a portion of the outlet region of the catheter is configured for insertion into a portion of the renal artery while maintaining blood flow through the source of arterial blood and the renal artery,
    wherein the outlet region of the catheter is configured for engagement within the patient's renal artery by selective occlusion of the renal artery such that blood exiting the lumen through the outlet port is substantially blocked from flowing out of the renal artery, and
    wherein the power source is configured for selective actuation to control a pressure and a rate of blood flow through the lumen and into the renal artery of the kidney.

2. The renal pump catheter system of claim 1, wherein the rotor of the catheter is an axial rotor.

3. The renal pump catheter system of claim 1, wherein the outlet region of the catheter is flexible.

4. The renal pump catheter system of claim 3, wherein the inlet region of the catheter is less flexible than the outlet region of the catheter.

5. The renal pump catheter system of claim 1, further comprising a mount that is positioned therein the first end of the inlet region of the catheter and is configured to prevent retrograde blood flow into the conduit from the inlet region.

6. The renal pump catheter system of claim 5, wherein the rotor of the catheter is configured for rotational movement about a longitudinal axis of the mount.

7. The renal pump catheter system of claim 1, further comprising means for controlling the pressure of the blood delivered to the outlet port such that the pressure is within a normal autoregulatory range of a perfusion pressure for the kidney.

8. The renal pump catheter system of claim 7, further comprising means for monitoring a pressure of the fluid proximate the outlet port of the catheter.

9. The renal pump catheter system of claim 8, wherein the pressure being monitored is the blood pressure within the renal artery.

10. The renal pump catheter system of claim 1, further comprising means for controlling a pressure of the blood delivered to the outlet port such that the pressure is higher than the normal autoregulatory range but lower than the pressure that will cause barotrauma of the kidney.

11. The renal pump catheter system of claim 10, further comprising means for monitoring a pressure of the fluid proximate the outlet port of the catheter.

12. The renal pump catheter system of claim 11, wherein the pressure being monitored is the blood pressure within the renal artery.

13. The renal pump catheter system of claim 1, further comprising means for determining a baseline renal function by monitoring a urine output of the patient.

14. The renal pump catheter system of claim 1, further comprising means for determining a baseline renal function by monitoring a blood pressure of the patient.

15. The renal pump catheter system of claim 1, further comprising means for determining a baseline renal function by monitoring at least one hormonal level of the patient.

16. The renal pump catheter system of claim 1, wherein the source of arterial blood is the patient's aorta.

* * * * *